United States Patent
Boss et al.

(10) Patent No.: US 12,005,066 B2
(45) Date of Patent: Jun. 11, 2024

(54) COBINAMIDE COMPOUNDS AS A CYANIDE, SULFIDE, OR METHANE-THIOL ANTIDOTE

(71) Applicants: The Regents of the University of California, Oakland, CA (US); The Regents of the University of Colorado, Denver, CO (US)

(72) Inventors: Gerard Boss, La Jolla, CA (US); Adriano Chan, La Jolla, CA (US); Matthew Brenner, La Jolla, CA (US); Sari Brenner Mahon, La Jolla, CA (US); Vikhyat Bebarta, Denver, CO (US)

(73) Assignees: The Regents of the University of California, Oakland, CA (US); The Regents of the University of Colorado, Denver, CO (US)

( * ) Notice: Subject to any disclaimer, the term of this patent is extended or adjusted under 35 U.S.C. 154(b) by 778 days.

(21) Appl. No.: 15/734,254

(22) PCT Filed: Jun. 4, 2019

(86) PCT No.: PCT/US2019/035353
§ 371 (c)(1),
(2) Date: Dec. 2, 2020

(87) PCT Pub. No.: WO2019/236552
PCT Pub. Date: Dec. 12, 2019

(65) Prior Publication Data
US 2021/0213031 A1 Jul. 15, 2021

Related U.S. Application Data

(60) Provisional application No. 62/680,208, filed on Jun. 4, 2018.

(51) Int. Cl.
*A61K 31/555* (2006.01)
*A61K 9/00* (2006.01)
*A61P 39/02* (2006.01)

(52) U.S. Cl.
CPC .......... *A61K 31/555* (2013.01); *A61K 9/0019* (2013.01); *A61P 39/02* (2018.01)

(58) Field of Classification Search
CPC .............................. A61K 31/555; A61P 39/02
See application file for complete search history.

(56) References Cited

U.S. PATENT DOCUMENTS

2015/0353590 A1 12/2015 Boss et al.

OTHER PUBLICATIONS

PCT International Search Report and Written Opinion for PCT Application No. PCT/US2019/035353 dated Sep. 27, 2019 (7 pages).
Fedosov et al., "Tetrazole Derivatives and Matrices as Novel Cobalamin Coordinating Compounds," Journal of Organometallic Chemistry, 2007, 692:1234-1242.
Johnson et al., "Identification of 5,6-Dimethylbenzimidazole as the Coα Ligand of the Cobamide Synthesized by *Salmonella typhimurium*," The Journal of Biological Chemistry, 1992, 267(19):13302-13305.
Waibel et al., "New Derivatives of Vitamin B12 Show Preferential Targeting of Tumors," Cancer Res, 2008, 68(8):2904-2911.

*Primary Examiner* — Barbara P Badio
(74) *Attorney, Agent, or Firm* — Eversheds Sutherland (US) LLP

(57) ABSTRACT

Methods and compositions for treating cyanide, sulfide, or methane-thiol exposure in a subject. The compositions may include one or more cobinamide compounds, such as an amino-tetrazole-cobinamide and/or a di-(amino-tetrazole)-cobinamide.

16 Claims, 4 Drawing Sheets

COBINAMIDE COMPOUNDS AS A CYANIDE, SULFIDE, OR METHANE-THIOL ANTIDOTE

CROSS REFERENCE TO RELATED APPLICATIONS

This application claims the priority benefit of PCT/US2019/035353 filed on Jun. 4, 2019 which claims the priority benefit to U.S. Provisional Patent Application No. 62/680,208, filed Jun. 4, 2018, the entire contents of which are incorporated herein by reference.

GOVERNMENT SPONSORSHIP

This invention was made with government support under grants U01NS58030, U01NS87964, and U54ES27698 awarded by the National Institutes of Health. The government has certain rights in the invention.

BACKGROUND

Cyanide is a highly toxic agent that inhibits mitochondrial cytochrome-c oxidase, thereby depleting cellular ATP. Cyanide exposure typically contributes to smoke inhalation deaths in fires, and could be used as a weapon of mass destruction. Cobalamin (vitamin $B_{12}$) binds cyanide with a relatively high affinity, and is used in Europe to treat smoke inhalation victims. Cobalamin also is FDA-approved for cyanide treatment in the USA. Cobinamide, the penultimate compound in cobalamin biosynthesis, binds cyanide with about $10^{10}$ greater affinity than cobalamin, and can be as effective when administered up to 5 minutes post-cyanide exposure as when given pre-exposure. Cobinamide also can be an effective intra- and/or extra-cellular nitric oxide scavenger.

Three cyanide antidotes are currently available: nitrites, thiosulfate, and hydroxocobalamin. All three drugs are approved only for intravenous (IV) administration, and thus are not suitable for treating mass casualties that could occur in certain circumstances, such as after a major industrial accident or a terrorist attack. In addition to inhalational exposure, people could be exposed to cyanide by eating or drinking cyanide-contaminated food or water. The currently available drugs for treating cyanide exposure, such as hydroxocobalamin (CYANOKIT® hydroxocobalamin for injection, MERIDIAN MEDICAL TECHNOLOGIES®, USA) and sodium thiosulfate/sodium nitrite (NITHIODOTE®, HOPE PHARMACEUTICALS, USA), have to be administered intravenously, thereby requiring competent medical personnel to administer the drugs properly to a subject immediately at the time and place of cyanide exposure. Additionally, intravenous administration is a time consuming method of administering an antidote.

Compared to hydroxocobalamin, cobinamide enjoys several advantages; for example, cobinamide may (i) bind two cyanide molecules (instead of only one), (ii) have an overall affinity for cyanide that is several orders of magnitude greater, and/or (iii) be several-fold more water soluble. Aquohydroxocobinamide (which may be generated on dissolving cobinamide in water), however, suffers from one or more disadvantages, such as the fact that (i) it may bind relatively tightly to proteins in the extracellular matrix (ECM) after intramuscular (IM) injection, and, therefore, is not absorbed well, if at all, and (ii) it may bind to clotting factors, which may potentially induce a disseminated intravascular coagulation-type syndrome.

Therefore, there remains a need for treating exposure to toxic agents, such as cyanide, sulfide, or methane thiol, that are safer, faster, and/or easier.

SUMMARY OF THE INVENTION

Provided herein are methods and pharmaceutical compositions for treating cyanide, sulfide, and/or methane thiol exposure in a subject, including methods and compositions that are faster and/or easier to administer than currently available methods and compositions, respectively. In some embodiments, the pharmaceutical compositions provided herein have improved safety profiles. The methods provided herein may neutralize cyanide, sulfide, and/or methane thiol in a subject caused by exposure to such compounds.

In some embodiments, the one or more cobinamide compounds provided herein overcome or reduce the one or more disadvantages associated with aquohydroxocobinamide by placing one or more organic ligands on the cobalt atom (FIG. 1). The one or more ligands may be relatively tightly bound. Cobinamide is closely related to cobalamin, and lacks a dimethylbenzimidazole ribonucleotide group (FIG. 1). Cobinamide can have different ligands coordinated to the cobalt atom, including those herein.

In one aspect, methods for treating cyanide, sulfide, and methane thiol exposure in a subject are provided. In some embodiments, the methods include administering a therapeutically effective amount of a cobinamide compound to a subject. A cobinamide compound may be a component of a pharmaceutical composition.

In some embodiments, the cobinamide compound is administered at a dose of about 1 mg/kg to about 600 mg/kg, about 1 mg/kg to about 500 mg/kg, about 1 mg/kg to about 400 mg/kg, about 1 mg/kg to about 300 mg/kg, about 1 mg/kg to about 200 mg/kg, about 1 mg/kg to about 100 mg/kg, about 1 mg/kg to about 75 mg/kg, about 1 mg/kg to about 50 mg/kg, about 1 mg/kg to about 24 mg/kg, or about 1 mg/kg to about 16 mg/kg.

In some embodiments, the pharmaceutical compositions provided herein are administered, or are formulated to be administered, by intramuscular injection to neutralize cyanide, sulfide, and/or methane thiol. The pharmaceutical compositions may be administered by intramuscular injection in order to rescue a subject from lethal poisoning by these toxic chemicals.

In some embodiments, the pharmaceutical compositions provided herein include one or more cobinamide compounds, and are formulated for delivery to a subject, wherein the pharmaceutical compositions are effective for treating a disease state in a subject caused or exacerbated by the presence of excess nitric oxide (NO) in the subject. In some embodiments, the pharmaceutical compositions provided herein also include cobalamin, or a biologically active derivative (e.g., analog) thereof.

In some embodiments, the pharmaceutical compositions provided herein include one or more cobinamide compounds, and are formulated for delivery (e.g., intramuscular delivery) to a subject, wherein the pharmaceutical compositions are effective to neutralize cyanide, sulfide, and/or methane thiol in the subject. In some aspects, the pharmaceutical composition also includes cobalamin, or a biologically active derivative (e.g., analog) thereof.

In some embodiments, the one or more cobinamide compounds include an amino-tetrazole-cobinamide, a di-(amino-tetrazole)-cobinamide, an acetyl-tetrazole-cobinamide, a di-(acetyl-tetrazole)-cobinamide, an acetyl-imidazole-cobinamide, a di-(acetyl-imidazole)-cobinamide, or a combination thereof. An example of an amino-tetrazole-cobinamide is 5-amino-tetrazole-cobinamide. An example of a di-(amino-tetrazole)-cobinamide is di-(5-amino-tetrazole)-cobinamide. An example of an acetyl-tetrazole-cobinamide is 5-acetyl-tetrazole-cobinamide. An example of a di-(acetyl-tetrazole)-cobinamide is di-(5-acetyl-tetrazole)-cobinamide. An example of an acetyl-imidazole-cobinamide is 4-acetyl-imidazole-cobinamide. An example of a di-(acetyl-imidazole)-cobinamide is di-(4-acetyl-imidazole)-cobinamide.

In some embodiments, the cobinamide compounds are safe and/or easy to administer by intramuscular injection to one or more subjects at the site of cyanide, hydrogen sulfide, or methane thiol poisoning. Compared to other forms of cobinamide that have been developed, the cobinamide compounds presented herein, in some embodiments, are much safer in subjects.

DETAILED DESCRIPTION

Figure 1:
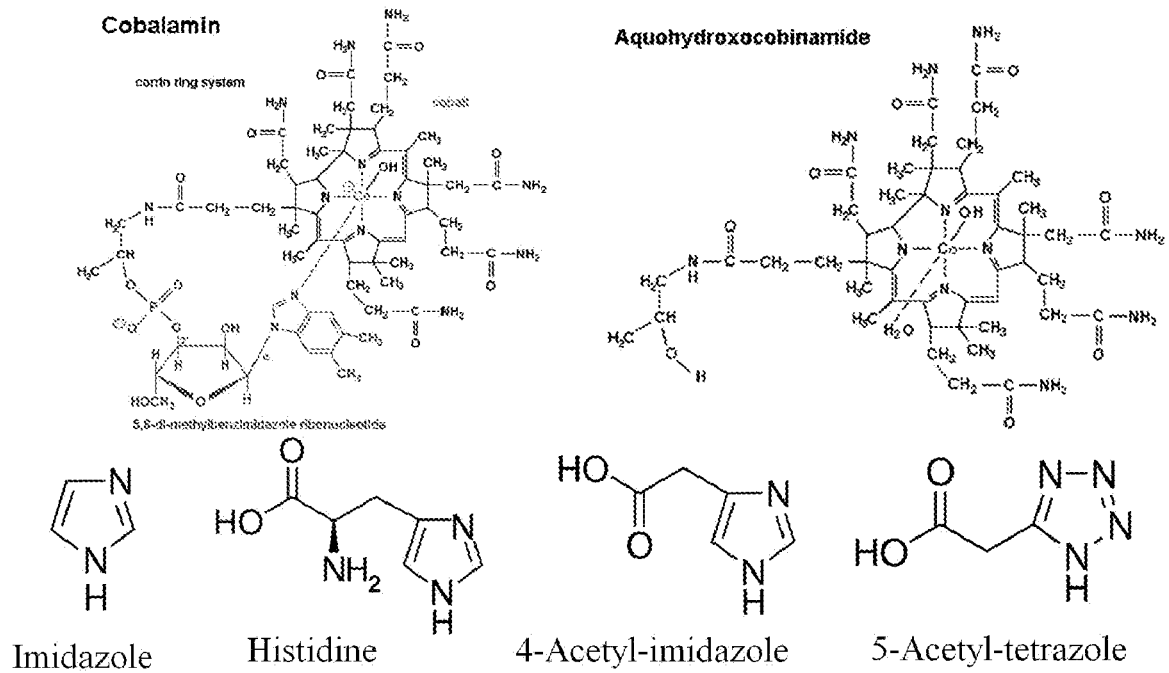
FIG. 1 depicts structures of hydroxocobalamin (top left), aquohydroxocobinamide (top right), and embodiments of ligands (bottom).

All publications, patents, and patent applications mentioned in this specification are hereby incorporated by reference to the same extent as if each individual publication, patent, or patent application was specifically and individually indicated to be incorporated by reference.

The practice of the present invention will employ, unless otherwise indicated, conventional techniques of molecular biology (including recombinant techniques), microbiology, cell biology, biochemistry and immunology, which are known to and employable by those of ordinary skill in the art.

DEFINITIONS

To facilitate understanding of the invention, a number of terms and abbreviations as used herein are defined below as follows:

When introducing elements of the present invention or the embodiment(s) thereof, the articles "a," "an," "the," and "said" are intended to mean that there are one or more of the elements. The terms "comprising," "including," and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone, or A and B in combination. The expression "A, B, and/or C" is intended to mean A alone, B alone, C alone, A and B in combination, A and C in combination, B and C in combination, or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from about 1 to about 6 should be considered to have specifically disclosed sub-ranges such as from about 1 to about 3, from about 1 to about 4, from about 1 to about 5, from about 2 to about 4, from about 2 to about 6, from about 3 to about 6 etc., as well as individual numbers within that range, for example, about 1, about 2, about 3, about 4, about 5, and about 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to pharmaceutically acceptable compositions, wherein the compositions include one or more cobinamide compounds, and, in some embodiments, also includes a pharmaceutically acceptable carrier. In some embodiments, the pharmaceutical composition is a combination.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which one or more cobinamide compounds may be administered. Such carriers may be sterile liquids, such as water and oils, including those of petroleum, animal, vegetable, or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, the phrases "effective amount," "therapeutically effective amount," or the like refer to an amount of one or more cobinamide compounds that is sufficient to treat or ameliorate, or in some manner reduce the symptoms associated with cyanide, sulfide, and/or methane thiol exposure. When used with reference to a method, the method is sufficiently effective to treat or ameliorate, or in some manner reduce the symptoms associated with cyanide, sulfide, and/or methane thiol exposure. For example, an effective amount in reference to cyanide, sulfide, and/or methane thiol exposure is that amount which is sufficient to neutralize, block, or prevent onset of the adverse effects of cyanide, sulfide, and/or methane thiol exposure; or if symptoms have begun, to palliate, ameliorate, stabilize, reverse or slow progression of the adverse effects, or otherwise reduce pathological consequences of cyanide, sulfide, and/or methane thiol exposure. In any case, an effective amount may be given in single or divided doses.

As used herein, the terms "treatment," "treating," or the like embrace at least an amelioration of the symptoms associated with cyanide, sulfide, and/or methane thiol exposure in the patient, where amelioration is used in a broad sense to refer to at least a reduction in the magnitude of a parameter, e.g. a symptom associated with cyanide, sulfide, and/or methane thiol exposure being treated. As such, "treatment," "treating," or the like also include situations where cyanide, sulfide, and/or methane thiol exposure, or at least symptoms associated therewith, are completely inhibited (e.g. prevented from happening) or stopped (e.g. terminated) such that the patient no longer suffers from the adverse effects associated with cyanide, sulfide, and/or methane thiol exposure, or at least the symptoms that characterize cyanide, sulfide, and/or methane thiol exposure.

The term "combination" refers to either a fixed combination in one dosage unit form, or a kit of parts for the combined administration where one or more cobinamide compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof, and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein, the phrase "cobinamide compound" refers to cobinamide and/or cobinamide derivatives. A cobalt atom of the cobinamide and cobinamide derivatives independently may be coordinated with no ligands or one or more ligands, for example, one ligand or two ligands. As used herein, the phrase "cobinamide derivative" refers to a biologically active derivative (e.g., analog) of cobinamide, such as a heterocyclic or heteropolycyclic compound that is (i) coordinated with a central cobalt atom, and (ii) substituted with two or more alkyl substituents (e.g., four to eight alkyl substituents) that include at least one polar functional group, such as an amide, an ester, an ether, carboxylic acid, etc. The heterocyclic or heteropolycyclic compound may include 4 heteroatoms, such as nitrogen, oxygen, etc. The one or more ligands of the cobinamide compounds disclosed herein may include any ligand that is capable of coordinating with the cobalt atom, such as an unsubstituted or substituted tetrazole, an unsubstituted or substituted imidazole, histidine, etc. As an example, a cobinamide compound may include 5-amino-tetrazole-cobinamide, which is cobinamide coordinated with one 5-amino-tetrazole ligand, or di-(5-amino-tetrazole)-cobinamide, which is cobinamide coordinated with two 5-amino-tetrazole ligands. As used herein, the phrase "amino-tetrazole" refers to a tetrazole moiety substituted at any one or more positions with (i) an amino moiety and/or (ii) a $C_1$-$C_3$ alkyl comprising an amino moiety. As used herein, the phrase "acetyl-tetrazole" refers to a tetrazole moiety substituted at any one or more positions with (i) an acetyl moiety and/or (ii) a $C_1$-$C_3$ alkyl comprising an acetyl moiety. As used herein, the phrase "acetyl-imidazole" refers to an imidazole moiety that is substituted at any one or more positions with (i) an acetyl moiety and/or (ii) a $C_1$-$C_3$ alkyl comprising an acetyl moiety.

Provided herein are pharmaceutical compositions that may include one or more cobinamide compounds, and methods of using the pharmaceutical compositions as a cyanide, sulfide, or methane-thiol antidote. In some embodiments, the one or more cobinamide compounds include one or more ligands, which may improve binding affinity and/or allow the one or more cobinamide compounds to be absorbed (completely or partially) after intramuscular injection. In some embodiments, the one or more cobinamide compounds have a low pKa for dissociation of one or more ionizable protons. In preferred embodiments, an unsubstituted or substituted tetrazole, which resembles an imidazole but has a pKa of 4.7 instead of 7.0, is the ligand of the one or more cobinamide compounds. When the one or more ligands includes amino-tetrazole and/or acetyl-tetrazole, the pKa of the nitrogen that coordinates to the cobalt may be about 4.9, which is about two orders of magnitude lower than for imidazole-containing cobinamides. This lower pKa can markedly increase acetyl-tetrazole and/or amino-tetrazole binding to cobinamide under physiological conditions.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Figure 2:
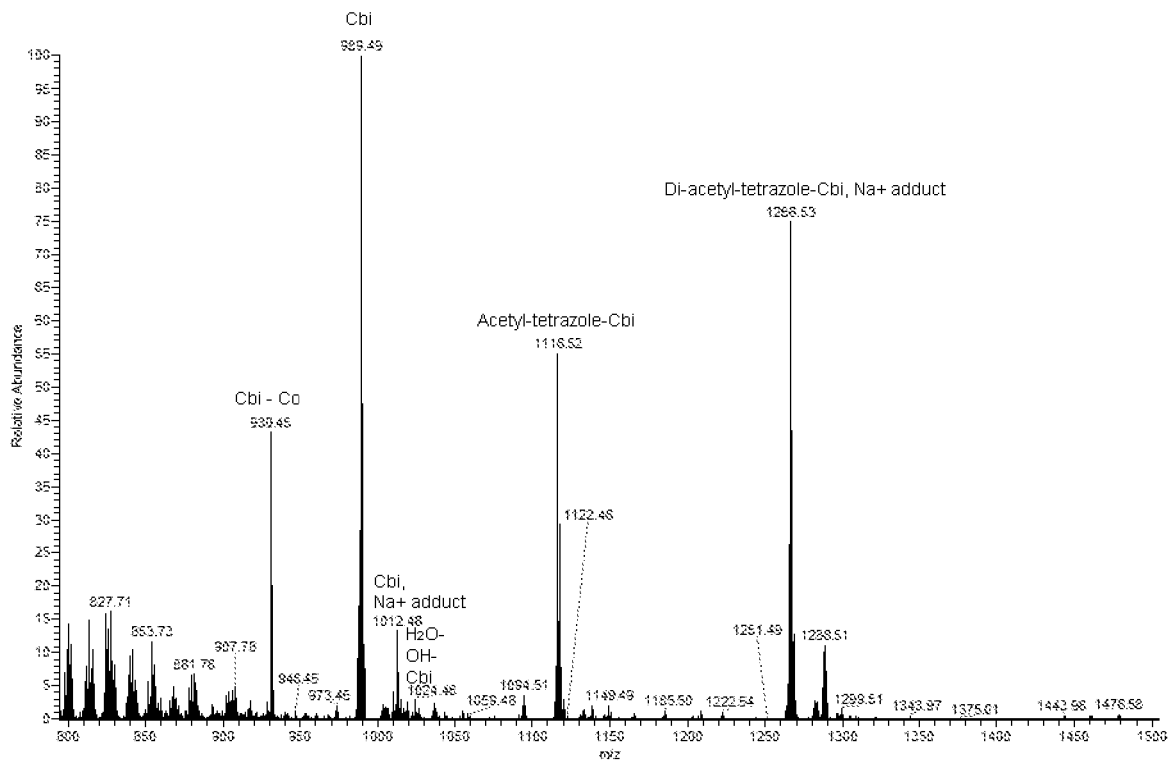
FIG. 2 depicts a mass spectrum of di-(acetyl-tetrazole)-cobinamide (DAcT-Cbi).
Figure 3:
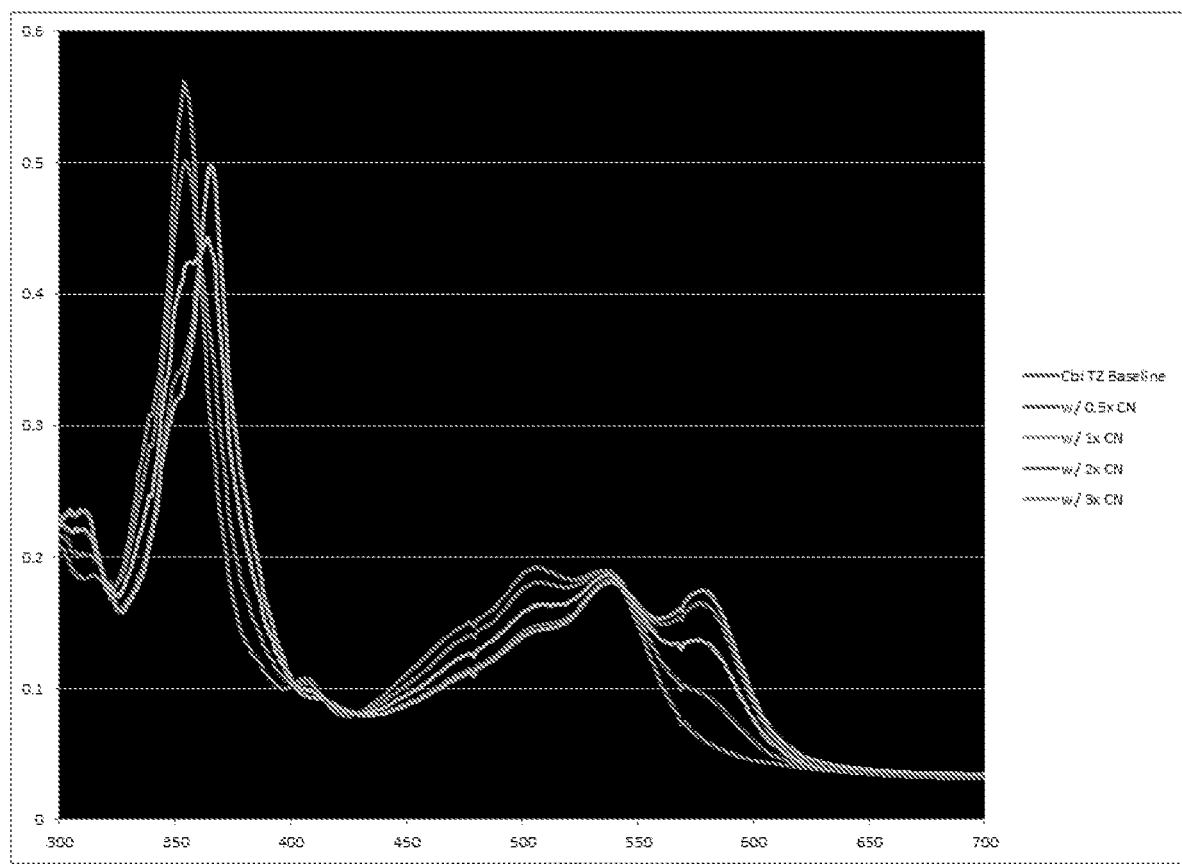
FIG. 3 depicts a UV-visible spectrum of DAcT-Cbi mixed with cyanide.

A di-(acetyl-tetrazole)-cobinamide (DAcT-Cbi) was synthesized and analyzed by mass spectroscopy. Peaks corresponding to acetyl-tetrazole-cobinamide and di-(acetyl-tetrazole)-cobinamide were detected (FIG. 2). Further, the effect of mixing DAcT-Cbi was investigated using UV-visible spectroscopy. A 25 μM solution of DAcT-Cbi was scanned from 300 nm to 700 nm, and then increasing concentrations of sodium cyanide were added to the DAcT-Cbi. At a 3× molar equivalent amount of cyanide, the cobinamide was fully saturated with cyanide. This was the same molar amount of cyanide required to fully saturate aquo-hydroxo-cobinamide; thus, the acetyl-tetrazole did not interfere with cyanide binding (FIG. 3).

It has been shown that the vitamin $B_{12}$ analog cobinamide is an effective cyanide antidote, and the initially-developed nitrocobinamide was well absorbed after intramuscular (IM) injection, and had the potential to treat mass casualties from cyanide gas inhalation. However, it seemed possible that even a safer form of cobinamide could be developed.

An exemplary cobinamide compound having a high safety profile was developed. The compound included two molecules of 5-amino-tetrazole bound to cobinamide, and is referred to herein as di-(5-amino-tetrazole)-cobinamide (DAmT-Cbi). Studies have shown that the major toxic effect of cobinamide is activation of the clotting cascade; generating a disseminated intramuscular coagulation-type syndrome with prolongation of the activated partial thromboplastin time and protime, and reduction in fibrinogen and the platelet count. With previous cobinamide formulations, more than half the animals died at doses of 300 mg/kg to 400 mg/kg. A range-finding toxicity study in rats for DAmT-Cbi was conducted, and, in the study, six animals (3 males and 3 females) were injected with 1200 and 1500 mg/kg of DAmT-Cbi. All animals were clinically normal and survived until 24 hours post injection, at which point they were euthanized and their blood was analyzed. At the highest dose (1500 mg/kg), a small increase in the aPTT occurred, but fibrinogen and the platelet count remained normal (Table 1).

TABLE 1

Blood analysis 24 hours post DAcT-Cbi injection
(* indicates normal range).

| Parameter | 1200 mg/kg | 1500 mg/kg |
|---|---|---|
| Hematocrit (33-45)* | 44.3 | 42.1 |
| White blood cell count (4-11) * | 6.22 | 7.4 |
| Platelet count (400-1200) * | 784 | 704 |
| Activated partial thromboplastin time (10.4-16.3) * | 28.6 | 27.1 |
| Protime (13.6-16.6) * | 16.1 | 16.4 |
| Fibrinogen (210-450) * | 412 | 318 |

Di-(amino-tetrazole)-cobinamide was well tolerated by animals, and this was likely due to the high binding affinity of the tetrazole group for the cobalt atom in cobinamide. Because of the relatively lower pKa of the ionizable hydrogen atom, the tetrazole ligands likely remain bound to cobinamide, even at physiological pH. Thus, very little unliganded cobinamide would be available to bind to plasma and/or cellular proteins, which is the likely mechanism of cobinamide toxicity.

Figure 4:
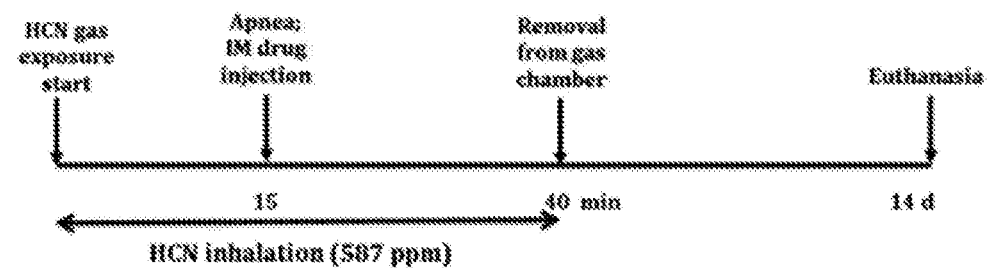
FIG. 4 depicts a schematic of a "Mouse Lethal Cyanide Inhalation Model" and results.
Figure 4:
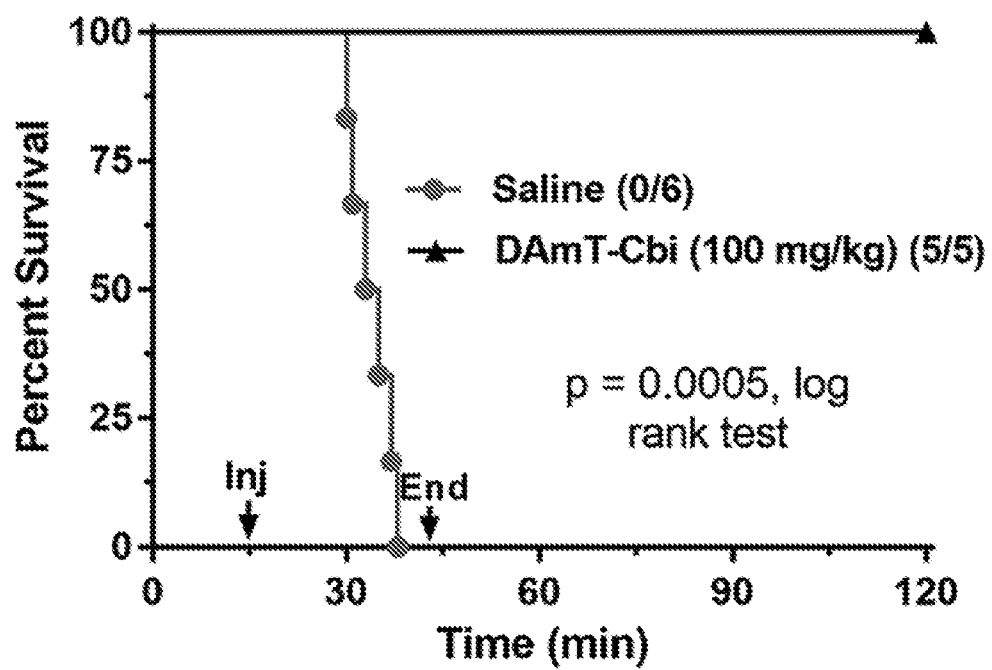

The efficacy of DAmT-Cbi was tested. DAmT-Cbi was shown to rescue mice from lethal cyanide poisoning (FIG. 4). Using the following cyanide-poisoning protocol/model; C57/B1 mice were exposed to 587 ppm HCN in a gas exposure chamber. After 15 minutes, they were removed from the chamber, and received an intramuscular injection of saline (circles) or the indicated amounts (100 mg/kg) of DAmT-Cbi. They were placed back in the chamber for an additional 25 minutes. All animals that received saline died over a relatively short time period, whereas 5 of 5 of those that received DAmT-Cbi (100 mg/kg) survived (p=0.0005 for difference between the two groups). Survivors were observed for at least two weeks, and all appeared normal during that time (FIG. 4). The human equivalent dose (HED) of 100 mg/kg in mice is 8 mg/kg. Additional tests showed that 4 of 4 pigs survived at 10 mg/kg DAmT-Cbi by intravenous administration when using the cyanide-poisoning model, whereas 7 of 8 control animals died. The human equivalent dose (HED) of 10 mg/kg in pigs is 9.1 mg/kg. Additional tests showed that 3 of 3 rabbits survived at 50 mg/kg DAmT-Cbi by intravenous administration when using a highly-monitored cyanide-poisoning model, whereas 100% lethality was observed in control animals. The human equivalent dose (HED) of 50 mg/kg in rabbits is 16 mg/kg. DAmT-Cbi was also effective against hydrogen sulfide and methyl mercaptan (methane thiol) in mice, rabbits, and pigs.

Figure 5:
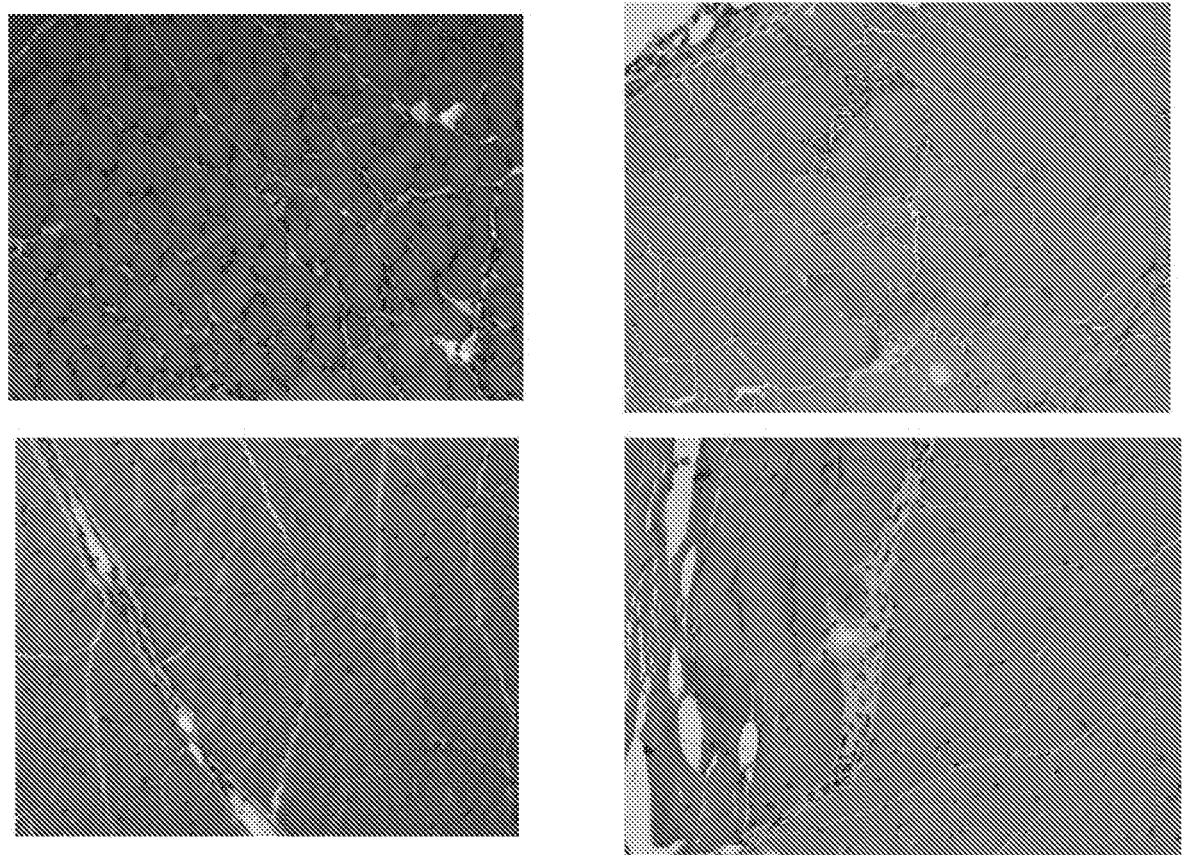
FIG. 5 depicts muscle biopsies from mice injected with di-(5-acetyl-tetrazole)-cobinamide.

Muscle biopsies from mice injected with DAmT-Cbi are shown in FIG. 5. The mice were injected with 50 μl of either saline (left) or 50 mM DAmT-Cbi (right). After 24 hours, the mice were euthanized, and the site of injection was fixed and stained with hematoxylin-eosin. Minimal to no toxic effect of the DAmT-Cbi was found.

The activated partial thromboplastin time (aPTT) of human plasma was determined after exposure to various drug compounds (Table 2). These data show that DAmT-Cbi caused the same small prolongation of the aPTT as hydroxocobalmin; the latter compound was very well tolerated by humans.

TABLE 2 aPTT of human plasma post drug exposure.

| Drug conc. | Control | Aquo-hydroxo-Cbi | Nitro-Cbi | Histidyl-Cbi | 4-acetyl-imidazole-Cbi | 5-acetyl-tetrazole-Cbi | 5-amino-tetrazole-Cbi | Dicyano-Cbi | Hydroxo-cobalamine |
|---|---|---|---|---|---|---|---|---|---|
| 0 | 35 | | | | | | | | |
| 300 μM | | >120 | 60 | 60 | 39 | 44 | 37 | 35 | 37 |
| 1 mM | | >120 | 110 | 110 | 41 | 55 | 43 | 36 | 44 |

TABLE 3

Safety Profiles of Several Cobinamide Formulations

| Species | Nitro-Cbi (mg/kg) | His-Cbi (mg/kg) | Di-(5-acetyl-tetrazole)-Cbi (mg/kg) | Di-(5-amino-tetrazole)-Cbi (mg/kg) |
|---|---|---|---|---|
| Mouse | 250 | 250 | 1000 | 3000 |
| Rat | 300 | 300 | >600 | >1200 |
| Dog | 15 | 15 | Not Tested | Not Tested |

("Nitro-Cbi" was cobinamide with two nitrite molecules bound; "His-Cbi" was cobinamide with two histidine molecules bound; "Di-(5-acetyl-tetrazole)-Cbi" was cobinamide with two 5-acetyl-tetrazole molecules bound; and "Di-(5-amino-tetrazole)-Cbi" was cobinamide with two 5-amino-tetrazole molecules bound.)

A large number of potential ligands were tested, and the results revealed that an imidazole or tetrazole derivative can be used; imidazole is the ligand bound in cobalamin. Three compounds, 4-acetyl-imidazole, 5-acetyl-tetrazole, and 5-amino-tetrazole, were all found to bind tightly to cobinamide, and to be absorbed rapidly after IM injection. All three cobinamide derivatives were very effective in mouse, rabbit, and pig models of cyanide poisoning when administered by IM injection. Moreover, the three derivatives were well tolerated in mice, but the amino-tetrazole derivative had the highest safety profile of the three ligands. Formal pharmacokinetic and toxicological studies of amino-tetrazole-cobinamide were conducted in rats, and this cobinamide derivative was found to be safe at a dose of 1500 mg/kg (Table 3).

The systemic safety profile of DAmT-Cbi was compared to that of nitro- and histidyl-cobinamide (Table 3). Mice, rats, and dogs were injected with the indicated amounts of the agents, generally by intramuscular route, unless the volume was too large and then the drugs were given by intraperitoneal injection. For nitro- and histidyl-cobinamide, the maximum tolerated dose (MTD) in mice and rats was determined to be 250 and 300 mg/kg, respectively, and in dogs to be 15 mg/kg. For DAmT-Cbi, the MTD in mice was determined to be 3000 mg/kg, and in rats to be 1500 mg/kg. The human equivalent dose (HED) of 3000 mg/kg in mice is 238 mg/kg, and HED of 1500 mg/kg in rats is 235 mg/kg, whereas the projected human dose is 8-24 mg/kg.

In order to generate the data of Table 3, mice, rabbits, and dogs were injected with the indicated cobinamide formulation at the indicated doses. For mice and rats, three males and three females were injected, and for dogs, one male and one female was injected. No clinical evidence of toxicity occurred at the indicated doses.

DAmT-Cbi and DAcT-Cbi had essentially the same efficacy profiles against cyanide, hydrogen sulfide, and methane thiol, but DAmT-Cbi had an overall better safety profile.

REFERENCES

1. Ann Emerg Med 64:612-619, 2014
2. Clin Toxicol 48: 709-717, 2010
3. Ann Emerg Med 55:352-363, 2010
4. Scientific Reports 6:20831, 2016 5. J. Med. Toxicol 12:370-379, 2016
6. Acad Emerg Med 24: 1088-1098, 2017
7. Exp Biol Med 231: 641-649, 2006
8. J. Med Chem 58: 1750-1759, 2015
9. Clin Toxicol 52: 490-497, 2014

What is claimed is:

1. A method for ameliorating one or more symptoms associated with cyanide exposure, sulfide exposure, or methane thiol exposure in a subject, comprising administering to the subject an effective amount of a pharmaceutical composition comprising an effective amount of one or more cobinamide compounds; wherein the one or more cobinamide compounds is selected from the group consisting of an amino-tetrazole-cobinamide, a di-(amino-tetrazole)-cobinamide, an acetyl-tetrazole-cobinamide, and a di-(acetyl-tetrazole)-cobinamide.

2. The method of claim 1, wherein the amino-tetrazole-cobinamide comprises 5-amino-tetrazole-cobinamide.

3. The method of claim 1, wherein the di-(amino-tetrazole)-cobinamide comprises di-(5-amino-tetrazole)-cobinamide.

4. The method of claim 1, wherein the acetyl-tetrazole-cobinamide comprises 5-acetyl-tetrazole-cobinamide.

5. The method of claim 1, wherein the di-(acetyl-tetrazole)-cobinamide comprises di-(5-acetyl-tetrazole)-cobinamide.

6. The method of claim 1, wherein the effective amount of the one or more cobinamide compounds is about 8 mg/kg to about 24 mg/kg.

7. The method of claim 1, wherein the pharmaceutical composition further comprises a pharmaceutically acceptable carrier to facilitate the amelioration of one or more symptoms.

8. The method of claim 1, wherein the pharmaceutical composition is a sterile solution or a sterile suspension.

9. A pharmaceutical composition comprising one or more cobinamide compounds, wherein the one or more cobinamide compounds is selected from the group consisting of an amino-tetrazole-cobinamide, a di-(amino-tetrazole)-cobinamide, an acetyl-tetrazole-cobinamide, and a di-(acetyl-tetrazole)-cobinamide.

10. The pharmaceutical composition of claim 9, wherein the amino-tetrazole-cobinamide comprises 5-amino-tetrazole-cobinamide.

11. The pharmaceutical composition of claim 9, wherein the di-(amino-tetrazole)-cobinamide comprises di-(5-amino-tetrazole)-cobinamide.

12. The pharmaceutical composition of claim 9, wherein the acetyl-tetrazole-cobinamide comprises 5-acetyl-tetrazole-cobinamide.

13. The pharmaceutical composition of claim 9, wherein the di-(acetyl-tetrazole)-cobinamide comprises di-(5-acetyl-tetrazole)-cobinamide.

14. The pharmaceutical composition of claim 9, wherein the pharmaceutical composition further comprises a pharmaceutically acceptable carrier.

15. The pharmaceutical composition of claim 9, wherein the pharmaceutical composition is a sterile solution or a sterile suspension.

16. The pharmaceutical composition of claim 9, wherein the pharmaceutical composition is formulated for intramuscular delivery.

* * * * *